United States Patent
Edelman et al.

(10) Patent No.: US 10,188,667 B2
(45) Date of Patent: *Jan. 29, 2019

(54) PHARMACEUTICAL COMPOSITIONS AND METHODS OF USE OF 4-PREGENEN-11β-17-21-TRIOL-3,20-DIONE DERIVATIVES

(71) Applicant: ALLERGAN, INC., Irvine, CA (US)

(72) Inventors: Jeffrey L. Edelman, Irvine, CA (US); Alissar Nehme, Mission Viejo, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/640,093

(22) Filed: Jun. 30, 2017

(65) Prior Publication Data

US 2018/0147217 A1    May 31, 2018

Related U.S. Application Data

(63) Continuation of application No. 14/485,335, filed on Sep. 12, 2014, now Pat. No. 9,717,743, which is a continuation of application No. 13/673,074, filed on Nov. 9, 2012, now Pat. No. 8,865,691.

(60) Provisional application No. 61/558,775, filed on Nov. 11, 2011.

(51) Int. Cl.
| | |
|---|---|
| *A61K 31/58* | (2006.01) |
| *A61K 31/56* | (2006.01) |
| *A61K 31/573* | (2006.01) |
| *C07J 7/00* | (2006.01) |
| *C07J 17/00* | (2006.01) |
| *C07J 31/00* | (2006.01) |
| *A61K 9/00* | (2006.01) |
| *C07J 5/00* | (2006.01) |
| *A61K 31/575* | (2006.01) |

(52) U.S. Cl.
CPC ............ *A61K 31/58* (2013.01); *A61K 9/0048* (2013.01); *A61K 31/56* (2013.01); *A61K 31/573* (2013.01); *C07J 5/0053* (2013.01); *C07J 7/008* (2013.01); *C07J 17/00* (2013.01); *C07J 31/006* (2013.01); *A61K 31/575* (2013.01); *A61K 2121/00* (2013.01)

(58) Field of Classification Search
None
See application file for complete search history.

(56) References Cited

U.S. PATENT DOCUMENTS

| | | |
|---|---|---|
| 3,484,436 A | 12/1969 | Cross et al. |
| 3,530,038 A | 9/1970 | de Flines et al. |
| 3,557,162 A | 1/1971 | Lens et al. |
| 3,984,544 A | 10/1976 | Casmer et al. |
| 4,242,334 A | 12/1980 | Alpermann et al. |
| 5,362,721 A | 11/1994 | Stache et al. |
| 6,395,721 B1 | 5/2002 | Robinson et al. |
| 8,865,691 B2 * | 10/2014 | Edelman .................. C07J 7/008 514/179 |
| 9,433,631 B2 | 9/2016 | Edelman et al. |
| 9,717,743 B2 * | 8/2017 | Edelman .................. C07J 7/008 |
| 2005/0245497 A1 | 11/2005 | Penfold et al. |
| 2008/0004246 A1 | 1/2008 | Bodor |
| 2008/0194468 A1 | 8/2008 | Bodor |
| 2009/0312724 A1 * | 12/2009 | Pipkin .................. A61K 9/0043 604/294 |
| 2013/0123223 A1 | 5/2013 | Edelman et al. |

FOREIGN PATENT DOCUMENTS

| | | |
|---|---|---|
| GB | 1202626 | 8/1970 |
| JP | 52-136157 | 11/1977 |
| JP | 53-15360 | 2/1978 |
| WO | 2005-099715 | 10/2005 |
| WO | 2006-017347 | 2/2006 |
| WO | 2007138113 | 12/2007 |
| WO | 2007138114 | 12/2007 |

OTHER PUBLICATIONS

Cantrill, Herbert et al, Comparison of In Vitro Potency of Corticosteroids with Ability to Raise Intraocular Pressure American Journal of Ophthalmology, Jun. 1975, 1012-1017, 79(6).
Cross, L.C. et al, Rules for the Nomenclature of Organic Chemistry, Section E: Stereochemistry, Pure & Appl. Chem., 1976, 11-30, 45.
Delasco Dermatologic Lab & Supply, Inc. Material Safety Data Sheet (MSDS) for Croton oil (Jan. 2008).
google.com Search for "croton oil painful" (https://www.google.com/search?q=croton+oil+painful&source=lnt&tbs=cdr%3A1%2Ccd_min%3A1%2F1%2F2000%2Ccc_max%3A11%2F1%2F2011& tbm=; retrieved Mar. 28, 2016).
Heinrich Stahl, Handbook of Pharmaceutical Salts, Properties, Selection, and Use, Handbook of Pharmaceutical Salts, Properties, Selection, and Use, 2002, 329-345, N/A.
International Search Report & Written Opinion dated Mar. 12, 2013 for PCT/US12/64296 filed Nov. 9, 2012 in the name of Allergan, Inc.
Kaoru Sato, Synthesis and Anti-inflammatory activity of hydrocortisone 17,21-diesters, Hidorokoruchizon 17,21-Diesters, Taishio Pharmaceuticals Co. Ltd., 1981, 365-372.

(Continued)

*Primary Examiner* — Anna Pagonakis
(74) *Attorney, Agent, or Firm* — Jonathan Bass

(57) ABSTRACT

The present invention relates to pharmaceutical compositions comprising 4-pregenen-11β-17-21-triol-3,20-dione derivatives, and their use as pharmaceuticals as modulators of the glucocorticoid receptors (GR) and/or the mineralocorticoid receptors (MR). The invention relates specifically to the use of these compounds and their pharmaceutical compositions to treat ocular conditions associated with the glucocorticoid receptors (GR) and/or the mineralocorticoid receptors (MR).

24 Claims, No Drawings

(56) References Cited

OTHER PUBLICATIONS

Matheson Tri-Gas, Inc. Material Safety Data Sheet (MSDS) for Pyridine (Dec. 11, 2008).
Muraviev, I.A., Pharmaceutical technology, Moscow: Medicine, 1980, 288, 1.
Oillab.Info "Croton oil" (http://www.oilab.info/node/23078; retrieved Mar. 16, 2016).
US Department of Health and Human Services Occupational Health Guideline for Ethyl Ether (Sep. 1976).
Villena C., et al., Ocular inflammation models by topical application: Croton-oil induced uveitis, Curr. Eye. Res., 1999, 3-9, 18 (1), AEulos Press.
Wilkinson, Jennifer et al, Compound Profiling Using a Panel of Steroid Hormone Receptor Cell-Based Assays, Journal of Biomolecular Screening, 2008, 755-765, 13(8).

\* cited by examiner

PHARMACEUTICAL COMPOSITIONS AND METHODS OF USE OF 4-PREGENEN-11β-17-21-TRIOL-3,20-DIONE DERIVATIVES

RELATED APPLICATION

This application is a continuation of U.S. patent application Ser. No. 14/485,335, filed Sep. 12, 2014, which is a continuation of U.S. patent application Ser. No. 13/673,074, filed Nov. 9, 2012, now U.S. Pat. No. 8,865,691, issued Oct. 21, 2014, which claims the benefit of U.S. Provisional Application Ser. No. 61/558,775, filed Nov. 11, 2011, the disclosures of which are hereby incorporated by reference in their entirety and serve as the basis of a priority and/or benefit claim for the present application.

FIELD OF THE INVENTION

The present invention relates to pharmaceutical compositions comprising 4-pregenen-11β-17-21-triol-3,20-dione derivatives, and their use as pharmaceuticals as modulators of the glucocorticoid receptors (GR) and/or the mineralocorticoid receptors (MR). The invention relates specifically to the use of these compounds and their pharmaceutical compositions to treat ocular conditions associated with the glucocorticoid receptors (GR) and/or the mineralocorticoid receptors (MR).

BACKGROUND OF THE INVENTION

Glucocorticoid (GC) agonists represent a class of anti-inflammatory compounds that are useful in treating multiple ocular conditions including elevated intraocular pressure, glaucoma, uveitis, retinal vein occlusions, macular degeneration, diabetic retinopathy, various forms of macular edema, post-surgical inflammation, inflammatory conditions of the palpebral and bulbar conjunctiva, cornea, and anterior segment of the globe, such as allergic conjunctivitis, ocular rosacea, dry eye, blepharitis, retinal detachment, meibomian gland dysfunction (MGD), superficial punctate keratitis, herpes zoster keratitis, iritis, cyclitis, selected infective conjunctivitis, corneal injury from chemical, radiation, or thermal burns, penetration of foreign bodies, allergy, or combinations thereof.

A potential use limiting and sight-threatening side-effect of traditional GC agonist therapies (e.g. fluocinolone acetonide) is ocular hypertension that is likely generated by an increased resistance of aqueous humor flow through the trabecular meshwork. The mechanism of GC agonist-induced outflow resistance and subsequent ocular hypertension is not well understood.

As such, GC modulation through agonist or antagonist activity of GC receptors that does not result in increased intraocular pressure or other side effects is needed in the art and is described herein.

SUMMARY OF THE INVENTION

It has now been discovered the use of a group of 4-pregenen-11β-17-21-triol-3,20-dione derivatives as potent and selective glucocorticoid receptors (GR) and/or the mineralocorticoid receptors (MR). As such, the compounds described herein are useful in treating a wide variety of disorders associated with modulation of the glucocorticoid receptors (GR) receptor or the mineralocorticoid receptors (MR). The term "modulator" as used herein, includes but is not limited to: receptor agonist, antagonist, inverse agonist, inverse antagonist, partial agonist, partial antagonist.

The present invention relates to pharmaceutical compositions comprising 4-pregenen-11β-17-21-triol-3,20-dione derivatives useful in treating one or more ocular conditions. Methods of treating one or more ocular conditions are also disclosed. Ocular conditions treated using compounds and/or formulations described herein include, but are not limited to, elevated intraocular pressure, glaucoma, uveitis, retinal vein occlusions, macular degeneration, diabetic retinopathy, various forms of macular edema, post-surgical inflammation, inflammatory conditions of the palpebral and bulbar conjunctiva, cornea, and anterior segment of the globe, such as allergic conjunctivitis, ocular rosacea, dry eye, blepharitis, retinal detachment, meibomian gland dysfunction (MGD), superficial punctate keratitis, herpes zoster keratitis, iritis, cyclitis, selected infective conjunctivitis, corneal injury from chemical, radiation, or thermal burns, penetration of foreign bodies, allergy, or combinations thereof.

The present invention relates to a method of treating a disorder associated with modulation of the glucocorticoid receptors (GR) and/or the mineralocorticoid receptors (MR), which comprises administering a therapeutically effective amount of a composition comprising a 4-pregenen-11β-17-21-triol-3,20-dione derivative. The compounds in accordance with the present invention are thus of use in medicine, for example in the treatment of humans with diseases and conditions that are alleviated by glucocorticoid or mineralocorticoid receptors modulation.

In one aspect, the invention provides a pharmaceutical composition of a 4-pregenen-11β-17-21-triol-3,20-dione derivative selected from the group of compounds from Table 1:

TABLE 1

| Compound | IUPAC name | Structure |
|---|---|---|
| 1 | (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl phenylacetate | 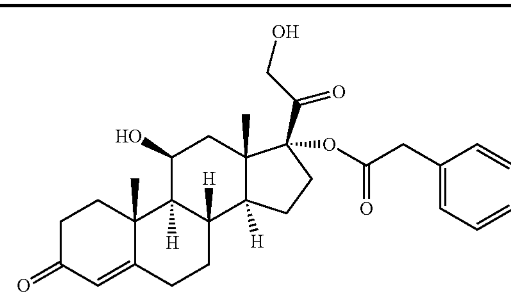 |

TABLE 1-continued

| Compound | IUPAC name | Structure |
|---|---|---|
| 2 | (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl butyrate | 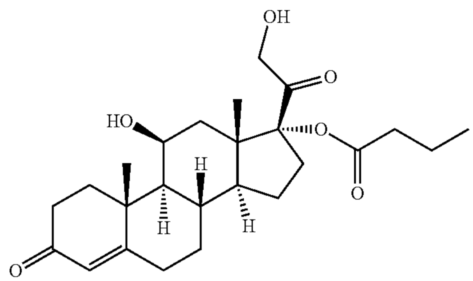 |
| 3 | (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl propionate | 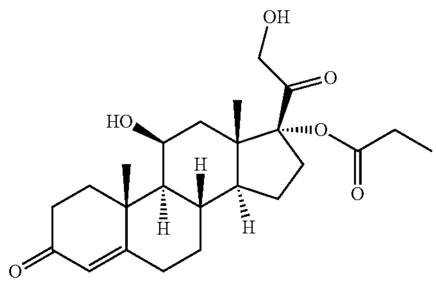 |
| 4 | (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl octanoate | 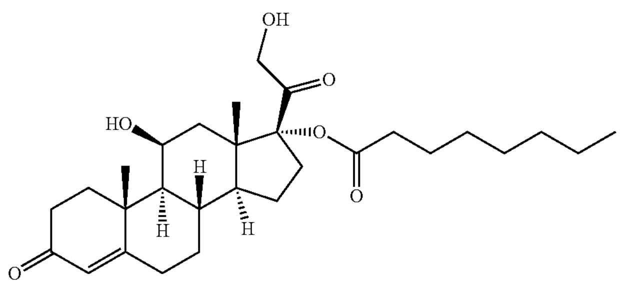 |
| 5 | (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl hexanoate | 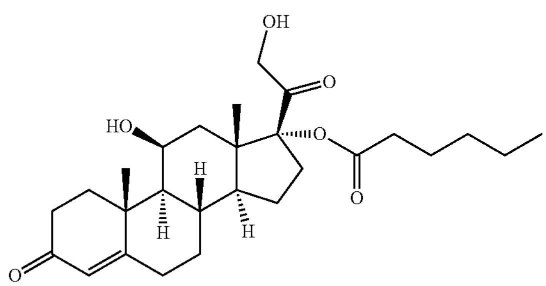 |
| 6 | (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl benzoate | 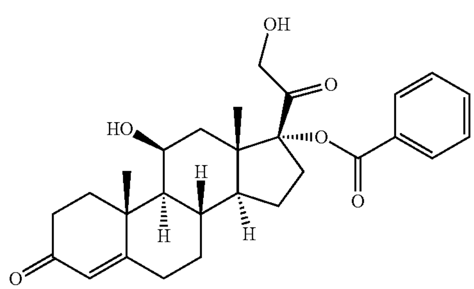 |

TABLE 1-continued

| Compound | IUPAC name | Structure |
|---|---|---|
| 7 | (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl heptanoate | 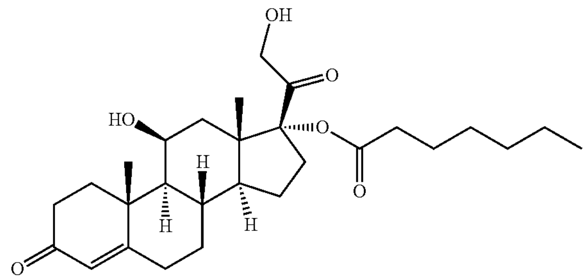 |
| 8 | (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl 2-methylpropanoate | 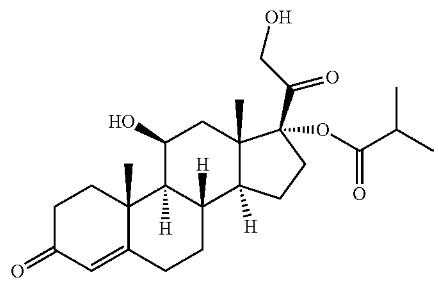 |
| 9 | (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl rel-cyclopentanecarboxylate | 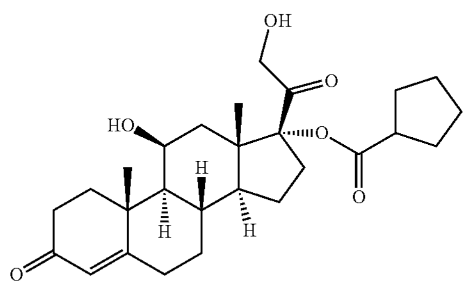 |

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Table 1 are able to form.

The acid addition salt form of a compound of the invention that occurs in its free form as a base can be obtained by treating the free base with an appropriate acid such as an inorganic acid, such as for example, hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahl & Camille G. Wermuth (Eds), Verlag Helvetica Chemica Acta-Zürich, 2002, 329-345).

The base addition salt form of a compound of the invention that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like. (Handbook of Pharmaceutical Salts, P. Heinrich Stahl & Camille G. Wermuth (Eds), Verlag Helvetica Chemica Acta-Zürich, 2002, 329-345).

Compounds of the invention and their salts can be in the form of a solvate, which is included within the scope of the present invention. Such solvates include for example hydrates, alcoholates and the like.

The compounds described herein are useful in treating a variety of ocular conditions including, but not limited to elevated intraocular pressure, glaucoma, uveitis, retinal vein occlusions, macular degeneration, diabetic retinopathy, various forms of macular edema, post-surgical inflammation, inflammatory conditions of the palpebral and bulbar conjunctiva, cornea, and anterior segment of the globe, such as allergic conjunctivitis, ocular rosacea, dry eye, blepharitis, retinal detachment, meibomian gland dysfunction (MGD), superficial punctate keratitis, herpes zoster keratitis, iritis, cyclitis, selected infective conjunctivitis, corneal injury from chemical, radiation, or thermal burns, penetration of foreign bodies, allergy, or combinations thereof.

In still another embodiment of the invention, there are provided methods for treating disorders associated with modulation of the glucocorticoid receptors (GR) and/or the mineralocorticoid receptors (MR). Such methods can be performed, for example, by administering to a subject in need thereof a therapeutically effective amount of at least one compound of Table 1, or any combination thereof, or pharmaceutically acceptable salts thereof.

In another embodiment, there are provided pharmaceutical compositions including at least one compound of Table 1 in a pharmaceutically acceptable carrier.

The compounds described herein may be administered at pharmaceutically effective dosages. Such dosages are normally the minimum dose necessary to achieve the desired therapeutic effect. Generally, such doses will be in the range of about 1 mg/day to about 1000 mg/day; more preferably in the range of about 10 mg/day to about 500 mg/day. In another example embodiment, the compound or compounds may be present in a composition or formulation in a range of about 0.5 mg/kg/day to about 100 mg/kg/day or about 1 mg/kg/day to about 100 mg/kg/day. However, the actual amount of the compound to be administered in any given case will be determined by a physician taking into account the relevant circumstances, such as the age and weight of the patient, the patient's general physical condition, the severity of ocular condition, and the route of administration. In some instances, dosing is evaluated on a case-by-case basis.

In another example embodiment, provided are pharmaceutical compositions including at least one compound in a pharmaceutically acceptable carrier. Pharmaceutical compositions can be used in the form of a solid, a solution, an emulsion, a dispersion, a micelle, a liposome, and the like, wherein the resulting composition contains one or more compounds described herein, as an active ingredient, in admixture with an organic or inorganic carrier or excipient suitable for enteral or parenteral applications. One or more compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Compounds described herein are included in pharmaceutical compositions in an amount sufficient to produce the desired effect upon the process or disease condition.

In another embodiment, the compounds described herein can be administered orally in any acceptable form, such as a tablet, liquid, capsule, powder and the like. However, other routes may be desirable or necessary, particularly if the patient suffers from nausea. Such other routes may include, without exception, transdermal, parenteral, subcutaneous, intranasal, intrathecal, intramuscular, intravenous, and intrarectal modes of delivery. Additionally, formulations may be designed to delay release of the active compound over a given period of time, or to carefully control the amount of drug released at a given time during the course of therapy.

Pharmaceutical compositions in a form suitable for oral use, for example, are administered as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing compounds described herein in admixture with non-toxic pharmaceutically acceptable excipients may also be manufactured by known methods.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required. Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

The actual amount of the compound to be administered in any given case will be determined by a physician taking into account the relevant circumstances, such as the severity of the condition, the age and weight of the patient, the patient's general physical condition, the cause of the condition, and the route of administration.

Described herein are compounds capable of modulating glucocorticoid receptors (GR) and/or mineralocorticoid receptors (MR). The compounds described can have greater GR activation and/or binding potency compared to a compound such as cortisol. As such, the compounds can efficiently treat ocular indications. The compounds can further be metabolized by esterase enzymes within the eye to form the natural agonist cortisol, thereby reducing the risk of ocular hypertension. The cortisol remaining within the eye and body is further metabolized to inactive compounds via naturally occurring dehydroxylases and other enzymes making this a safe therapeutic approach.

In patients, the naturally occurring endogenous GC agonist cortisol (hydrocortisone) has a minimal effect on intraocular pressure when applied locally via eye drops compared to synthetic GCs such as dexamethasone, prednisolone, and fluorometholone (Cantrill et al., 1975). Further support of the overall superior safety of cortisol as a therapeutic is the fact that various topical hydrocortisone formulations are currently sold over the counter directly to consumers.

Without wishing the bound to any particular theory, it was surprisingly discovered that the presently described compounds can have more glucocorticoid receptor modulation than cortisol because of the modification to the 17-position of the cortisol molecule.

As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the compounds are mixed with an inert solid diluent, for example, calcium carbonate, calcium phosphate or kaolin. They may also be in the form of soft gelatin capsules wherein the compounds are mixed with water or an oil medium, for example, peanut oil, liquid paraffin, or olive oil.

The compounds described herein can also be administered as an ophthalmically acceptable formulation or composition. A liquid which is ophthalmically acceptable is formulated such that it can be administered topically to the eye. The comfort should be maximized as much as possible, although sometimes formulation considerations (e.g. stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in ophthalmic compositions described herein include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations described herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In one example embodiment, an ophthalmic composition as described herein may have ingredients used in the following amounts listed in Table 2.

TABLE 2

| Ingredient | Amount (% w/v) |
| --- | --- |
| active ingredient | about 0.001-5 |
| preservative | 0-0.10 |
| vehicle | 0-40 |

TABLE 2-continued

| Ingredient | Amount (% w/v) |
| --- | --- |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

In other embodiments, the ophthalmically acceptable liquid can be formulated for intraocular injection. The compounds described herein can be formulated as a liquid, gel, paste, cream, oil. Further, the compounds can be formulated into sustained release or controlled release intraocular implants comprising biodegradable polymers such as polylactic acid, poly glycolic acid, combinations thereof and the like.

Some exemplary compositions can include a combination of two or more compounds as described herein. Different ratios of compounds can be formulated depending on a particular ocular condition or set of conditions being treated.

Since individual subjects may present a wide variation in severity of symptoms and each composition has its unique therapeutic characteristics, the precise mode of administration and dosage employed for each subject is left to the discretion of the practitioner.

DETAILED DESCRIPTION

It is to be understood that both the foregoing general description and the following detailed description are exemplary and explanatory only and are not restrictive of the invention claimed. As used herein, the use of the singular includes the plural unless specifically stated otherwise.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diastereoisomeric isomers, chromatographic separation may be employed.

EXAMPLE 1

Glucocorticoid Receptor Transactivation Potencies for Cortisol and 17-ester Derivatives Glucocorticoid receptor (GR) activation potency was assessed using a HeLa cell line containing the MMTV-bla reporter (MMTV-bla HeLa CELLSENSOR®, Invitrogen Corp., Carlsbad, Calif.). This cell line was stably transfected with an expression construct containing β-lactamase cDNA under control of the MMTV response element previously identified as a glucocorticoid receptor response element.

Results from one experiment performed in duplicate for 9 compounds and the control compound, dexamethasone, are summarized in Table 3. All assays were performed as 10-point dose responses using a half log-fold dilution series starting with a maximum compound concentration of 100 nM. The compounds were incubated for 5 hours. The activation of endogenous GR leads to expression of the reporter β-lactamase which is detected by the conversion of a FRET substrate in a ratiometric assay format. This functional assay allows for measurement of receptor agonism by compounds and can be used to determine compound potency and selectivity. Assay reproducibility was determined by calculating Z' values for untreated versus maximum stimulation. The Z' value was greater than 0.6, indicating good reproducibility of the assay format.

Several compounds showed dose-dependent stimulation of the GR signaling pathway (Table 3). Compounds of Table 1 showed about 30-fold greater potency compared to the parent molecule cortisol.

TABLE 3

Glucocorticoid receptor potency. Shown are the $EC_{50}$ (nM) and Z' values for the control compound, dexamethasone, and compounds tested in agonist mode.

| Compound | EC50 (nM) GR | % Activation at 100 nM | Z' |
|---|---|---|---|
| 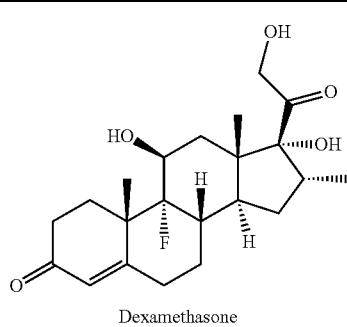 Dexamethasone | 1.05 | Control Compound | 0.87 |
| 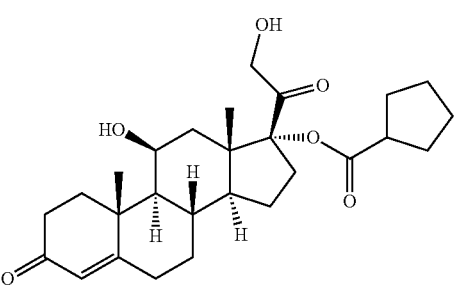 | 1.35 | 88 | 0.87 |
| 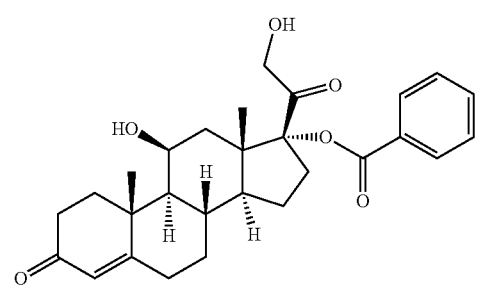 | 1.41 | 85 | 0.87 |
| 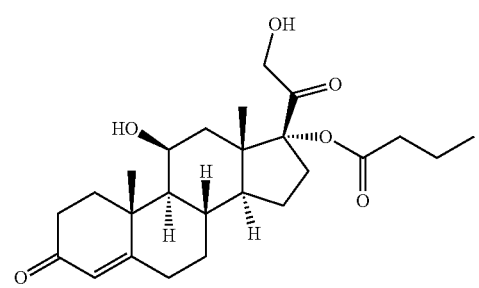 | 1.97 | 86 | 0.87 |

TABLE 3-continued
Glucocorticoid receptor potency. Shown are the $EC_{50}$ (nM) and Z' values for the control compound, dexamethasone, and compounds tested in agonist mode.
| Compound | EC50 (nM) GR | % Activation at 100 nM | Z' |
|---|---|---|---|
| 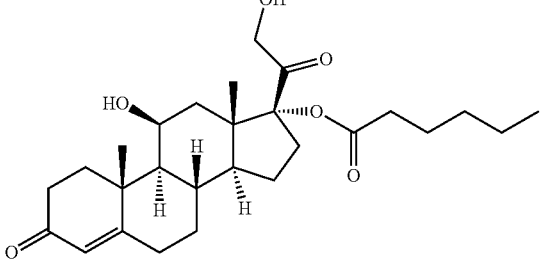 | 3.25 | 65 | 0.87 |
| 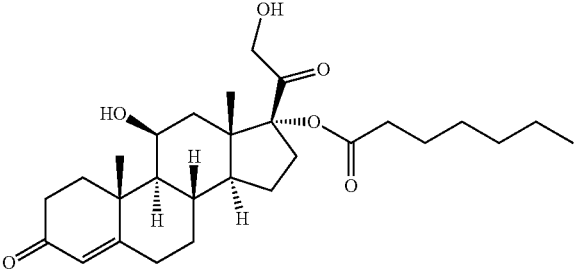 | 6.04 | 47 | 0.87 |
| 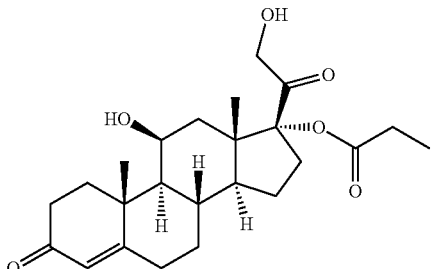 | 6.31 | 85 | 0.87 |
| 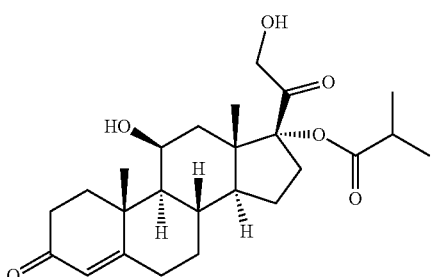 | 7.07 | 84 | 0.87 |
| 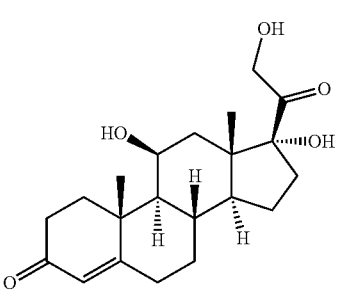<br>cortisol | 41.6 | 43 | 0.87 |

TABLE 3-continued

Glucocorticoid receptor potency. Shown are the $EC_{50}$ (nM) and Z' values for the control compound, dexamethasone, and compounds tested in agonist mode.

| Compound | EC50 (nM) GR | % Activation at 100 nM | Z' |
|---|---|---|---|
| [cortisol 17-heptanoate structure] | >100 | 15 | 0.87 |
| [cortisol 17-phenylacetate structure] | >100 | 5 | 0.87 |

EXAMPLE 2

Mineralocorticoid Receptor Transactivation Potencies for Cortisol and 17-ester Derivatives Mineralocorticoid receptor (MR) activation potency was assessed using a HEK 293T cell line containing the UAS-bla reporter (UAS-bla HEK 293T CELLSENSOR®). This cell line was stably cotransfected with an expression construct containing β-lactamase cDNA under control of the GAL4 Upstream Activator Sequence (UAS) and another expression construct encoding for the fusion protein GAL4(DBD)-MR(LBD). Results for one experiment performed in duplicate for 9 compounds and the control compound, aldosterone, in agonist mode are summarized in Table 4. All assays were performed as 10-point dose responses using a half log-fold dilution series starting with a maximum compound concentration of 100 nM. The compounds were incubated for 16 hours. The activation of the fusion protein GAL4(DBD)-MR(LBD) leads to expression of the reporter β-lactamase which is detected by the conversion of a FRET substrate in a ratiometric assay format. This functional assay allows for measurement of receptor agonism by compounds and can be used to determine compound potency and selectivity. Assay reproducibility was determined by calculating Z' values for untreated versus maximum stimulation. The Z' value was greater than 0.6, indicating good reproducibility of the assay format. Several compounds showed dose-dependent stimulation of the MR signaling pathway (Table 4).

TABLE 4

Mineralocorticoid receptor potency. Shown are the $EC_{50}$ (nM) and Z' values for the control compound, aldosterone, and all 10 compounds tested in agonist mode.

| Compound | EC50 (nM) GR | % Activation at 100 nM | Z' |
|---|---|---|---|
| [Aldosterone structure] Aldosterone | 0.47 | Control Compound | 0.77 |

TABLE 4-continued

Mineralocorticoid receptor potency. Shown are the $EC_{50}$ (nM) and Z' values for the control compound, aldosterone, and all 10 compounds tested in agonist mode.

| Compound | EC50 (nM) GR | % Activation at 100 nM | Z' |
|---|---|---|---|
| [structure] | 2.85 | 81 | 0.77 |
| [structure] cortisol | 2.90 | 75 | 0.77 |
| [structure] | 2.94 | 77 | 0.77 |
| [structure] | 3.17 | 76 | 0.77 |
| [structure] | 5.27 | 72 | 0.77 |

TABLE 4-continued
Mineralocorticoid receptor potency. Shown are the $EC_{50}$ (nM) and Z' values for the control compound, aldosterone, and all 10 compounds tested in agonist mode.
| Compound | EC50 (nM) GR | % Activation at 100 nM | Z' |
|---|---|---|---|
| 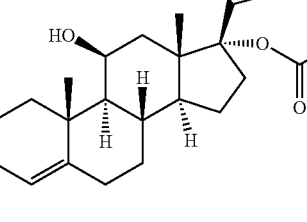 | 5.68 | 64 | 0.77 |
| 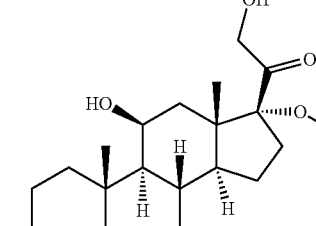 | 7.46 | 62 | 0.77 |
| 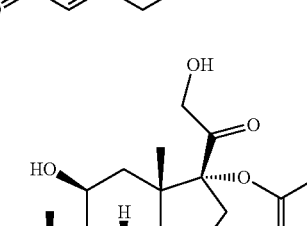 | 9.29 | 56 | 0.77 |
| 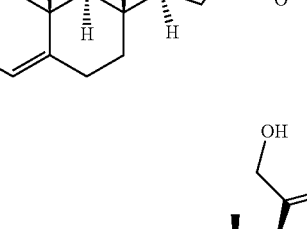 | 15.6 | 62 | 0.77 |
| 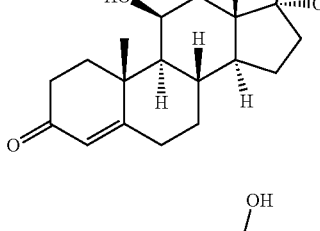 | >100 | 27 | 0.77 |

EXAMPLE 3

Treating Elevated Intraocular Pressure

A 58 year old male visits his ophthalmologist for a routine check-up. The physician discovers that the patient exhibits an elevated intraocular pressure and is at high risk for future complications. The patient is instructed to apply a topical liquid formulation containing one of the compounds in Table 1 once daily to each eye.

The patient returns for a follow-up visit three months later. Upon measuring intraocular pressure, it is noted that the patient now exhibits a reduced intraocular pressure.

EXAMPLE 4

Treating Ocular Irritation

A 38 year old male visits his ophthalmologist complaining of irritation in his right eye. The physician discovers that the patient's right eye is inflamed and red. The patient is instructed to apply a topical liquid formulation containing one of the compounds in Table 1 twice daily to the right eye.

The patient returns for a follow-up visit a week later. Upon inspection of the right eye, it is noted that the patient's eye is no longer red and the patient indicates that the irritation is gone.

Unless otherwise indicated, all numbers expressing quantities of ingredients, properties such as molecular weight, reaction conditions, and so forth used in the specification and claims are to be understood as being modified in all instances by the term "about."

Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of treating an ocular condition associated with glucocorticoid and or mineralocorticoid receptor modulation which comprises topically administering to a patient in need thereof, a pharmaceutical composition comprising a therapeutically effective amount of at least one compound selected from:
 (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl phenylacetate;
 (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl butyrate;
 (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl propionate;
 (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl octanoate;
 (8S,9S,10R,11S,13S,14S,17R)-17-Glycoloyl-11-hydroxy-10,13-dimethyl-3-oxo-2,3,6,7,8,9,10,11,12,13,14,15,16,17-tetradecahydro-1H-cyclopenta[a]phenanthren-17-yl hexanoate;
 (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl benzoate;

(8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl heptanoate;
(8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl 2-methylpropanoate; and
(8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl cyclopentanecarboxylate,
and further comprising carboxymethylcellulose, sodium phosphate, citrate buffer, and sodium chloride,
and having a pH from about 4.5 to 7.5.

2. The method according to claim 1 wherein the ocular condition is selected from elevated intraocular pressure, glaucoma, uveitis, retinal vein occlusions, macular degeneration, diabetic retinopathy, various forms of macular edema, post-surgical inflammation, inflammatory conditions of the palpebral and bulbar conjunctiva, cornea, and anterior segment of the globe, allergic conjunctivitis, retinal detachment, superficial punctate keratitis, herpes zoster keratitis, iritis, cyclitis, selected infective conjunctivitis, corneal injury from chemical, radiation, or thermal burns, penetration of foreign bodies, allergy, and combinations thereof.

3. The method according to claim 1 wherein the ocular condition is selected from ocular rosacea, dry eye, blepharitis, meibomian gland dysfunction.

4. The method according to claim 1 wherein the compound is:
(8S,9S, 10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren- 17-yl benzoate.

5. The method according to claim 1 wherein the compound is:
(8S,9,10R,11S,13S,14S,17R)-17-Glycoloyl-11-hydroxy-10,13-dimethyl-3-oxo-2,3,6,7,8,9,10,11,12,13,14,15,16,17-tetradecahydro-1H-cyclopenta[a]phenanthren-17-yl hexanoate.

6. The method according to claim 1 wherein the compound is:
(8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl octanoate.

7. The method according to claim 1 wherein the compound is:
(8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro- 1H-cyclopenta[a]phenanthren-17-yl phenylacetate.

8. The method according to claim 1 wherein the compound is:
(8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl butyrate.

9. The method according to claim 1 wherein the compound is:
(8S,9S,10R,11S,13S,14S,17R)-17-glycoloyl-11-hydroxy-10,13-dimethyl-3oxo-2,3,6,7,8,9,10,11,12,13,14,15,16,17-tetradecahydro- 1H-cyclopenta[a]phenanthren-17-yl propionate.

10. The method according to claim 1 wherein the compound is:
(8S,9S,10R,11S,13S,14,S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl heptanoate.

11. The method according to claim 1 wherein the compound is
(8S,9S,10R,11S,13S,14S, 17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl2-methylpropanoate.

12. The method according to claim 1 wherein the compound is
(8S,9S,10R,11S,13S, 14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl cyclopentanecarboxylate.

13. A method of treating an ocular condition associated with glucocorticoid and or mineralocorticoid receptor modulation which comprises topically administering to a patient in need thereof, a pharmaceutical composition comprising a therapeutically effective amount of at least one compound selected from:
(8S,9S,10R,11S,13S,14S,17R)-17-glycoloyl-11-hydroxy-10,13 -dimethyl-3 -oxo-2,3,6,7,8,9,10,11,12,13,14,15, 16,17-tetradecahydro-1H-cyclopenta[a]phenanthren-17-yl phenylacetate;
(8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl butyrate;
(8S,9S,10R,11S,13S,14S,17R)-17-glycoloyl-11-hydroxy-10,13 -dimethyl-3 -oxo-2,3,6,7,8,9,10,11,12,13,14,15, 16,17-tetradecahydro-1H-cyclopenta[a]phenanthren-17-yl propionate;
(8S,9S,10R,11S,13S,14S,17R)-17-glycoloyl-11-hydroxy-10,13 -dimethyl-3 -oxo-2,3,6,7,8,9,10,11,12,13,14,15, 16,17-tetradecahydro-1H-cyclopenta[a]phenanthren-17-yl octanoate;
(8S,9S,10R,11S,13S,14S,17R)-17-Glycoloyl-11-hydroxy-10,13 -dimethyl-3 -oxo-2,3,6,7,8,9,10,11,12,13,14,15,16,17-tetradecahydro-1H-cyclopenta[a]phenanthren-17-yl hexanoate;
(8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl benzoate;
(8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl heptanoate;
(8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl 2-methylpropanoate; and
(8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl cyclopentanecarboxylate;
and further comprising carboxymethylcellulose, mannitol, sodium phosphate, and citrate buffer;
and having a pH from about 4.5 to 7.5.

14. The method according to claim 13 wherein the ocular condition is selected from elevated intraocular pressure, glaucoma, uveitis, retinal vein occlusions, macular degeneration, diabetic retinopathy, various forms of macular edema, post-surgical inflammation, inflammatory conditions of the palpebral and bulbar conjunctiva, cornea, and anterior segment of the globe, allergic conjunctivitis, retinal detachment, superficial punctate keratitis, herpes zoster keratitis, iritis, cyclitis, selected infective conjunctivitis, corneal injury from chemical, radiation, or thermal burns, penetration of foreign bodies, allergy, and combinations thereof.

15. The method according to claim 13 wherein the ocular condition is selected from ocular rosacea, dry eye, blepharitis, meibomian gland dysfunction.

16. The method according to claim 13 wherein the compound is:
    (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl benzoate.

17. The method according to claim 13 wherein the compound is:
    (8S,9S,10R,11S,13S,14 S,17R)-17-Glycoloyl-11-hydroxy-10,13-dimethyl-3-oxo-2,3,6,7,8,9,10,11,12,13,14,15,16,17-tetradecahydro-1H-cyclopenta[a]phenanthren-17-yl hexanoate.

18. The method according to claim 13 wherein the compound is:
    (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl octanoate.

19. The method according to claim 13 wherein the compound is:
    (8S,9S, 10R, 11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl phenylacetate.

20. The method according to claim 13 wherein the compound is:
    (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl butyrate.

21. The method according to claim 13 wherein the compound is:
    (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl propionate.

22. The method according to claim 13 wherein the compound is:
    (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl heptanoate.

23. The method according to claim 13 wherein the compound is
    (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl 2-methylpropanoate.

24. The method according to claim 13 wherein the compound is
    (8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl cyclopentanecarboxylate.

* * * * *

UNITED STATES PATENT AND TRADEMARK OFFICE
CERTIFICATE OF CORRECTION

PATENT NO. : 10,188,667 B2
APPLICATION NO. : 15/640093
DATED : January 29, 2019
INVENTOR(S) : Jeffrey L. Edelman et al.

It is certified that error appears in the above-identified patent and that said Letters Patent is hereby corrected as shown below:

In the Specification

In Column 5, Line 56, delete "Stahl&" and insert -- Stahl & --, therefor.

In Column 5, Line 57, delete "Chemica" and insert -- Chimica --, therefor.

In Column 5, Line 65, delete "Stahl&" and insert -- Stahl & --, therefor.

In Column 5, Line 66, delete "Chemica" and insert -- Chimica --, therefor.

In the Claims

In Column 22, Line 39, in Claim 1, delete "and or" and insert -- and/or --, therefor.

In Column 22, Line 45, in Claim 1, delete "13 -dimethyl-3 -oxo-" and insert -- 13-dimethyl-3-oxo- --, therefor.

In Column 22, Line 53, in Claim 1, delete "13 -dimethyl-3 -oxo-" and insert -- 13-dimethyl-3-oxo- --, therefor.

In Column 22, Line 65, in Claim 1, delete "13 -dimethyl-3 -oxo-" and insert -- 13-dimethyl-3-oxo- --, therefor.

In Column 23, Line 2, in Claim 1, delete "13 -dimethyl-3 -oxo-" and insert -- 13-dimethyl-3-oxo- --, therefor.

In Column 23, Line 10, in Claim 1, delete "13 -dimethyl-3 -oxo-" and insert -- 13-dimethyl-3-oxo- --, therefor.

In Column 23, Line 32, in Claim 4, delete "9S, 10R," and insert -- 9S,10R, --, therefor.

Signed and Sealed this
Twenty-sixth Day of March, 2019

Andrei Iancu
*Director of the United States Patent and Trademark Office*

CERTIFICATE OF CORRECTION (continued)
U.S. Pat. No. 10,188,667 B2

In Column 23, Lines 34-35, in Claim 4, delete "phenanthren- 17-yl" and insert -- phenanthren-17-yl --, therefor.

In Column 23, Line 38, in Claim 5, delete "9," and insert -- 9S, --, therefor.

In Column 23, Lines 46-47, in Claim 6, delete "phenanthren- 17-yl" and insert -- phenanthren-17-yl --, therefor.

In Column 23, Line 52, in Claim 7, delete "-tetradecahydro- 1H-" and insert -- -tetradecahydro-1H- --, therefor.

In Column 23, Lines 58-59, in Claim 8, delete "phenanthren- 17-yl" and insert -- phenanthren-17-yl --, therefor.

In Column 23, Line 63, in Claim 9, delete "-3oxo-" and insert -- -3-oxo- --, therefor.

In Column 23, Line 64, in Claim 9, delete "-tetradecahydro- 1H-" and insert -- -tetradecahydro-1H- --, therefor.

In Column 24, Line 1, in Claim 10, delete "14,S," and insert -- 14S, --, therefor.

In Column 24, Line 7, in Claim 11, delete "14S, 17R" and insert -- 14S,17R --, therefor.

In Column 24, Line 10, in Claim 11, delete "-yl2-" and insert -- -yl 2- --, therefor.

In Column 24, Line 13, in Claim 12, delete "13S, 14S," and insert -- 13S,14S, --, therefor.

In Column 24, Line 18, in Claim 13, delete "and or" and insert -- and/or --, therefor.

In Column 24, Line 24, in Claim 13, delete "13 -dimethyl-3 -oxo-" and insert -- 13-dimethyl-3-oxo- --, therefor.

In Column 24, Line 32, in Claim 13, delete "13 -dimethyl-3 -oxo-" and insert -- 13-dimethyl-3-oxo- --, therefor.

In Column 24, Line 36, in Claim 13, delete "13 -dimethyl-3 -oxo-" and insert -- 13-dimethyl-3-oxo- --, therefor.

In Column 24, Line 40, in Claim 13, delete "13 -dimethyl-3 -oxo-" and insert -- 13-dimethyl-3-oxo- --, therefor.

In Column 25, Line 17, in Claim 17, delete "14 S," and insert -- 14S, --, therefor.

In Column 25, Line 29, in Claim 19, delete "9S, 10R, 11S," and insert -- 9S,10R,11S, --, therefor.